US007153250B2

(12) United States Patent
Takizawa et al.

(10) Patent No.: US 7,153,250 B2
(45) Date of Patent: Dec. 26, 2006

(54) METHOD FOR MANAGING EXERCISE FOR FUNCTION RECOVERY AND MUSCLE STRENGTHENING

(76) Inventors: Shigeo Takizawa, 24-5, Shounandai 4-Chome, Fijisawa-Shi (JP) 252-0804; Kyoko Takizawa, 24-5, Shounandai 4-Chome, Fijisawa (JP) 252-0804

( * ) Notice: Subject to any disclaimer, the term of this patent is extended or adjusted under 35 U.S.C. 154(b) by 0 days.

(21) Appl. No.: 10/451,858

(22) PCT Filed: Jun. 25, 2001

(86) PCT No.: PCT/JP01/05383

§ 371 (c)(1),
(2), (4) Date: Oct. 29, 2003

(87) PCT Pub. No.: WO02/50738

PCT Pub. Date: Jun. 27, 2002

(65) Prior Publication Data

US 2004/0067819 A1 Apr. 8, 2004

(30) Foreign Application Priority Data

Dec. 21, 2000 (JP) ............................ 2000-388445

(51) Int. Cl.
*A63B 71/00* (2006.01)
(52) U.S. Cl. ...................... 482/148; 434/255; 434/258; 434/262; 434/433; 482/23
(58) Field of Classification Search ................ 482/148, 482/23; 434/247, 255, 258, 262, 433; 128/898; 273/440; 73/379.01
See application file for complete search history.

(56) References Cited

U.S. PATENT DOCUMENTS

| | | | |
|---|---|---|---|
| 4,988,981 A | | 1/1991 | Zimmerman et al. |
| 5,078,152 A | | 1/1992 | Bond et al. |
| 5,759,043 A | * | 6/1998 | Craig .......................... 434/247 |
| 5,791,905 A | * | 8/1998 | Larson, Jr. .................. 434/247 |
| 5,955,879 A | | 9/1999 | Durdle et al. |
| 6,017,606 A | * | 1/2000 | Sage et al. ..................... 428/68 |
| 6,165,143 A | | 12/2000 | van Lummel |
| 6,177,940 B1 | | 1/2001 | Bond et al. |
| 6,733,421 B1 | | 5/2004 | Jones |
| 6,743,167 B1 | * | 6/2004 | Balkin et al. ................ 600/137 |
| 6,750,194 B1 | | 6/2004 | Isfort et al. |
| 6,770,029 B1 | | 8/2004 | Iliff |
| 6,772,012 B1 | | 8/2004 | Ricart et al. |
| 6,774,885 B1 | * | 8/2004 | Even-Zohar ................ 345/156 |
| 6,776,743 B1 | | 8/2004 | Hur |
| 6,780,142 B1 | | 8/2004 | Takizawa et al. |
| 6,814,708 B1 | | 11/2004 | Jennings |
| 2004/0127335 A1 | | 7/2004 | Watterson et al. |
| 2004/0198555 A1 | | 10/2004 | Anderson et al. |
| 2004/0220017 A1 | | 11/2004 | Gordon et al. |

FOREIGN PATENT DOCUMENTS

| | | |
|---|---|---|
| JP | 952134 | 2/1996 |
| JP | 1182202 | 6/2003 |

OTHER PUBLICATIONS

U.S. Appl. No. 10/456,888, filed Jun. 3, 2003, Takizawa et al.
U.S. Appl. No. 10/779,125, filed Feb. 12, 2004, Takizawa et al.
U.S. Appl. No. 10/779,126, filed Feb. 12, 2004, Takizawa et al.
U.S. Appl. No. 10/464,003, filed Jun. 17, 2003, Takizawa.
U.S. Appl. No. 10/311,917, filed Mar. 4, 2003, Takizawa.
Yoshiko Morita, Enforcement of the Motivative exercise by the Takizawa Rehabilitation Program, Paper presented at: The 37th Japanese Association of Rehabilitation Medicine, Academic meeting. Tokyo. Jul. 24, 2000: Session 3-K-42.
Endo S, Makita M, Nagasawa H, Takizawa K, Kobayashi K, Shoji J (May, 1999) Rehabilitation Training With Two Simple Training Machines., Proceedings of 13th International Congress of the World Confederation for Physical Therapy, 539.
The Development of Devices for the MOTIVATIVE Exercise of Impaired Extremities. Paper presented at: the CSUN Conference. Los Angeles. Mar. 22. 2000: Session 166.
Takizawa, S, Keeping the Elderly in Motion, 2000. Reha. Management international Medical World Communications. Los Angels. 48.
Takizawa S, Kijima H, Kimura T, et al, The study of the motivative exercise and the Takizawa program by the 21st Century Rehabilitation Study Meeting in Japan. CSUN's sixteenth Annual International Conference. Los Angeles. Mar. 22, 2001: Session 163.
Takizawa, S, Kimura. T, Kijima, H, Takizawa K, et al. Ambulation from bedridden (The case report of a bedridden inpatient of double-hemiplegia. ISPRM. (1). 2001, Ferrarese, Monduzzi Editore, 743-746.
Takizawa, S, Kimura, T, Kijima, H, Okamoto, Y, Nagaoka, K, Morita, Y, Endo, S, Nagasawa, H, Makita, M. Takizawa, K (2001). Biophilia Rehabilitation and Proposition of the solution to the aging crisis. ISPRM. (1). Ferrarese, Monduzzi Editore. 729-736.
Takizawa, Shigeo. Rika Wada and Toshihiro Tachibana-(Nov. 2002) The Supplementary Examination of the Rehabilitation by the Program Developed to the Disabled Patients, International Biophilia Rehabilitation Conference Proceedings, 2002, (1) 38.
An Application of the Civil Technology to the Sustainable Aged Society, Biophilia Rehabilitation Journal, 2-1, 2004, p. 1-24.
Takizawa, Shigeo, Control System of Rehabilitation and Muscle Power Strength Training, Web proc. of 3rd Joint Congress on Disability and Biophilia Rehabilitation Academy, Sep. 18. 2004, http://www.jstage.jst.go.jp/browse/ibr/-char/en.

* cited by examiner

*Primary Examiner*—Lori Amerson

(57) ABSTRACT

A method includes: providing an exercise administration list containing a name column, an exercise group column, and an exercise date column; identifying an exercise person in need of exercise and a group of exercises for the person based on the exercise administration list; appointing an exercise administrator for managing exercise; confirming by the exercise administrator exercise working contents for the exercise person based on the exercise administration list; arranging by the exercise administrator devices used for performing the exercise working contents; confirming the exercise date; and thereby managing by the exercise administrator the exercises by the exercise person for function recovery and muscle strengthening.

9 Claims, No Drawings

METHOD FOR MANAGING EXERCISE FOR FUNCTION RECOVERY AND MUSCLE STRENGTHENING

This application is the U.S. National Phase under 35 U.S.C. §371 of International Application PCT/JP01/05383, filed Jun. 25, 2001, which claims priority to Japanese Patent Application No. 2000-388445, filed Dec. 21, 2000. The International Application was not published under PCT Article 21(2) in English.

FIELD OF INVENTION

This invention is a method for managing rehabilitation exercises and muscle power strengthening that enables a person, including an elderly and/or a physically impaired person, who requires the rehabilitation with physical therapies to recover and improve and/or strengthen a body's impaired function.

Additionally, this is a Control System of training by the Takizawa method and the motivative exercise for an elderly and/or a physically impaired person to perform.

BACKGROUND INVENTION

There is the rehabilitation with physical therapies to improve, recover and/or strengthen impaired body functions of an elderly and/or a physically impaired person.

There is the rehabilitation to improve, recover and/or strengthen the body functions that decreased due to remaining in a motionless state such as seen in astronauts. The exercises of the rehabilitation are divided into a passive exercise and an active exercise.

Namely, the rehabilitation is an exercise centering on a passive exercise where a physical therapist rehabilitates a patient individually.

It is also an active assistive exercise where a patient moves his or her impaired finger and/or hand by himself or herself excluding extremities, or an active exercise where a patient of good physical condition practices gymnastics and moves a desired part of a body as indicated by a therapist, such as a physical therapist.

Those methods of physical therapies were put in practice and administered by physical therapists who coordinate the exercise under the guidance of a physician, or patients exercised with active exercises under supervision.

Physical therapists check a patient's physical condition and decide what is suitable rehabilitation for each patient depending on the physical therapist's experience in order to the physician's prescription (e.g. rehabilitation, training, exercise, etc.).

A physical or a physical therapist mentally prepares and assembles contents of the rehabilitation with physical therapies for each patient.

In the case where the caregivers rehabilitate a patient at home, the caregiver performs the passive exercise following the advice of a physician and/or a physical therapist.

In this applicant, the Motivative exercise is defined as the movement of a functional extremity leads the movement of the impaired extremity by the use of devices and the Takizawa method is formed in order to perform the rehabilitation and muscle power strengthening to rehabilitate and to strengthen the muscle power with the Motivative exercise predominantly.

Additionally, this applicant has reported the principle of the Takizawa method for rehabilitation and the Motivative exercise as follows:

The Development of Devices for the MOTIVATIVE Exercise of Impaired Extremities. Paper presented at: the CSUN Conference, Los Angeles, Mar. 22, 2000; Session 166;

The Rehabilitation Trial to Reacquire Walking from Bedridden Patients at the Bedridden Elderly Hospital, Journal of the Japanese Clinical Orthopedic Association, Vol. 23, NO. 2 JUNE, 1998: 186–191;

The Development of Devices for the Motivative Exercise of Impaired Extremities. The 4678 Journal of Kouseihukusi (Welfare), the 4833rd Jiji press. May 17, 2000: 2–5.

This applicant has invented the devices related to the Motivative exercise such as lower extremities' exercise devices, upper extremities' exercise devices, and walkers.

Lower extremities' exercise devices are such as:

the registration of utility model JP2004587 DEVICE OF DORSIFLEXION AND PLANTAR FLEXION OF ANKLES AND KNEES;

the design patent registered JP997739 LOWER EXTREMITYS FUNCTION TRAINING DEVICE; and the design patent registered JP1096056 LOWER EXTREMITYS FUNCTION TRAINING DEVICE.

Upper extremities' exercise device is a requested patent, such as the PCT/JP00/04062 MOTIVATIVE EXERCISE AND LIFTING AID DUAL DEVICE for example.

Devices for standing and walking are such as:

the registration of utility model JP 1895489 WALKER;

the registration of utility model JP 1901372 TALIPES EQUINES-INVERSION RESTORATION;

the design patent registered JP 882110 MEDICAL SOCK;

the design patent registered JP 952134 WALKER; and the design patent registered JP 1008033 BATHROOMS CHAIR.

Also the JP S 1085325 LIFT and the trademarked AID CUSHION, JP3351881 are related devices that are registered by the Japanese Patent Office.

Furthermore, this applicant is applying for patents for the following devices to be used to realize the Motivative exercise such as:

the patent application H06-29447 Walker;

the patent application H11-358206 Lower extremities' exercise device;

the patent application 2000-180958 the Motivative exercise device for lower extremities;

the patent application PCT/JP99/07115 Lower extremities' exercise device;

the patent application PCT/JP00/03978 Motivative exercise device for lower extremities; and the patent application PCT/JP00/04062 Motivative exercise combined lift.

The physical therapist performs and manages the patient's rehabilitation individually under a doctor's guidance and refers to the medical rehabilitation chart depending upon the patient's varying diseases.

Though a caregiver takes care of a patient at home and performs rehabilitation exercises, such as passive exercise with the advice of doctor or a physical therapist, there can be a feeling of anxiety if the rehabilitation exercises are opposite.

The Takizawa method and Motivative exercise do not need easy administration for enforcement by other physical therapists because the Takizawa method and Motivative exercise are performed by individual physical therapists.

The applicant announced the papers that had explained, "What kind of devices are used", "What kind of effect taken in the case of using the devices" or "How to execute".

The applicant did not previously explain the control system.

In order to work smoothly anywhere, the control system is required to recognize and generalize the effect of a particular physical therapist's rehabilitation that centers on the Motivative exercise.

This invention offers a method for managing exercises for function recovery and muscle strengthening in order to dissolve the disadvantages of the previous method.

BRIEF SUMMARY OF THE INVENTION

The disclosure defined by this invention is composed of the following:

The first method of this invention has the following characteristics:

A planner entrusts to control exercises for a specified trainee(s) in any exercise group to an optional manager or managers by using a list, which is named "Exercise administration list", which is divided into "a name column"; "exercise columns", which have several specified exercise listed; and "exercise date columns".

After the commission of said "Exercise administration list", said manager(s) check the individual rehabilitation or training contents for a trainee(s) who is specified in the name column in order to prepare the devices for exercises which are filled in the exercise columns.

Said managers check and arrange the date of the exercises in one of the exercise date columns.

However the managers who have been entrusted by the planner can control the exercises of a specified trainee (s).

The second method of this invention has the following characteristics:

A planner of the Takizawa method and the Motivative exercise entrusts to control the Takizawa method and the Motivative exercise for a specified trainee(s) in any exercise group to an optional manager by using a list, which is named "Exercise administration list", which is divided into "a name column"; "exercise columns", which have several specified exercises for the Takizawa method and the Motivative exercise listed; and "exercise date columns".

After the commission of said "Exercise administration list", said manager(s) check the individual rehabilitation or training contents for a trainee(s) who is specified in the name column in order to prepare the devices for exercises which are filled in the exercise columns.

Said manager(s) checks and arrange the date to perform the exercises in one of the exercise date columns.

However the managers who have been entrusted by the planner can control the Takizawa method and the Motivative exercise of a specified trainee (s).

The third method of the this invention has the following characteristics:

A planner entrusts to control exercises for a specified trainee(s) in any exercise group to an optional manager or managers by using a list, which is named "Exercise control list", which is divided into "a name column" and "exercise columns", which have several specified exercises listed and a list, which is named "Performance Days List" that is divided into "name columns" and "exercise date columns".

After the commission of both said "Exercise control list" and said "Performance Days List", said manager(s) check the individual rehabilitation or training contents for a trainee(s) who is specified in the name column in order to prepare the devices for exercises which are filled in the exercise columns on the "Exercise control list". The manager(s) check and arrange the date of the exercises in one of the exercise date columns and the name of the trainee in one of the name columns on the "Performance Days List".

However the managers who have been entrusted by the planner can control the exercise of a specified trainee (s).

The fourth method of this invention has the following characteristics:

A planner entrusts an optional manager or managers to control the Takizawa method and the Motivative exercise for a specified trainee(s) in any exercise group by using a list, which is named "Exercise control list", which is divided into "a name column" and "exercise columns", which have several specified exercises listed and a list, which is named "Performance Days List" that is divided into "name columns" and "exercise date columns".

After the commission of both said "Exercise control list" and said "Performance Days List", said manager(s) check the individual rehabilitation or training contents for a trainee(s) who is specified in the name column in order to prepare the devices for exercises which are filled in the exercise columns on the "Exercise control list". Said manager(s) check and arrange the date of the exercises in one of the exercise date columns and the name of the trainee in one of the name columns on the "Performance Days List".

However the managers who have been entrusted by the planner can control the Takizawa method and the Motivative exercise of a specified trainee (s).

At present, a physical therapist rehabilitates a physically impaired person or patient with a joint range of motion exercise by the passive exercise, a muscle strength training and/or thermo therapy individually.

The physical therapist controls the rehabilitation by filling in a medical chart.

In this specification, a person trainee includes a physically impaired person or patient.

In the case of performing exercises, which are standardized for any facility (in the case of performing exercises in one's own home, any home), it is characteristics that this invention enable to control and to enforce rehabilitation and muscular power strength training and/or the Takizawa method and Motivative exercise of many trainees by using a list to control exercises or "Exercise administration list" or both a list to control exercises or "Exercise control list" and a list to administrate days to perform exercises or "Performance Days List".

Performing exercises including rehabilitation and muscle power strengthening and/or the Takizawa method and the Motivative exercise are enforced types of training with assistance by any trainee under an indication of one planner or manager, any manager who is indicated by a planner or any manager who is a planner.

Although, when a caregiver cares for a physically impaired person in their home, the caregiver feels the anxiety of performing the rehabilitation exercise, which may be a passive exercise, if it is correct.

The method for managing the rehabilitation has characteristics that enable the caregiver to correctly and safely perform the rehabilitation and muscle power strengthening and/or the Takizawa method and the Motivative exercise by using devices that can be prepared easily.

When there is an excessive amount of trainees by one manager, the planner assigns different managers to the persons under training.

It is desirable to be a planner that is an expert in rehabilitation medicine such as a physician or a physical therapist.

The planner can make a manager control the rehabilitation and muscular power strength training, centering on the Motivative exercise.

It is possible that a manager can become a planner by receiving a certain education.

Mainly elderly and physically impaired persons perform exercises in order to improve, recover and/or strength the function as a trainee(s), although, generally the elderly and healthy person can perform the Motivative exercise in order to maintain their health as a trainee(s).

Furthermore, the Motivative exercise is the movement of a healthy extremity leads with movement of an impaired extremity through the help of devices and can be defined as a mix of self and assisted training in this invention.

Persons do the Motivative exercise while sitting upright, straight position.

The Motivative exercise can replace some parts of the passive exercise, which is performed by a physical therapist.

A planner or manager can perform an assistive "Motivative exercise" while a patient performs the Motivative exercise.

And the Takizawa method formed by the applicant is the working method of function recovery and also muscular power strength exercise that centers on the Motivative exercise for elderly patients who have a disuse syndrome and have impairments.

The definition of the Takizawa method was defined as follows:

When patients who have joint contracture and/or flexion of extremities can be rehabilitated by the range of motion exercises for a trunk and paralyzed joint and/or extremity are rehabilitated in the absence of pain using the range of motion exercises while maintaining a sitting position;

it proceeds for patients who have a joint contracture and/or a flexion to secure a straight upright sitting position early by using a cushion or cushions in the Takizawa method; and rehabilitation for patients who have joint contracture and/or flexion of extremities are advanced early by keeping a sitting position through the use of cushions with the absence of pain in the case of the rehabilitation that contains both range of motion exercises and the muscle power strengthening training.

The Takizawa method is categorized; therefore the assistant and/or care person can operate the Takizawa method with the guidance of experts, such as physical therapists and/or occupational therapists.

Also, an expert such as a physical therapist or an occupational therapist can enforce the method with many patients.

The idea to motivate a patient's will is made within the Motivative exercise for lower extremities.

An example of the idea to motive a patient's will is when patients not only perform an active exercise with a weight band for a load and swing exercise for a lower extremities by themselves for a functional extremity but also an assistive exercise of lower extremities with the weight band for the load and swing exercise for a lower extremity even if they cannot move their own impaired extremity by themselves.

When the Motivative exercise is enforced following the method, thermo therapy may be necessary to remove pain during the exercises.

Thus, the Takizawa method includes and defines that thermo therapy, while sitting, must be enforced.

This invention is related and offers a method for managing rehabilitation exercises and muscle power strengthening and/or the Takizawa method for rehabilitation and Motivative exercise.

DETAILED DESCRIPTION OF THE INVENTION

This applicant describes the first embodiment of this Invention as following.

First, a list is named an "Exercise administration list".

The "Exercise administration list" in which a "name column", "exercise columns" and "exercise date columns" as a "main column" and a "remarks column(s)" are laid out properly for use in this embodiment as a document.

Then, the name column consists of a "trainee name column" and a "planner name column".

The exercise columns consist of "detailed exercise columns" with the types of exercises that are set up in multiple steps, in which types of exercises and/or a type of thermo therapy is listed and "sets of exercise columns" in which the number of repetitions and length of enforcement time period for thermo therapy are registered.

In the sets of exercise columns, length of the application for performing thermo therapy and the number of repetitions for describing of amount of kinetic momentum is clearly indicated.

The exercise columns consist of combinations with "detailed exercise columns" and the sets of exercise columns.

A part of the main column consists of multiple rows of "exercise date columns" and a "name column".

A "remarks column(s)" is used for information such as an address, ages and any distinction of the dementia.

The administration of rehabilitation and muscle power strengthening is managed, depending on the steps of a procedure and technique with using an "Exercise administration list" as follows.

A planner specifies an optional trainee and confirms that the trainee is able to keep a sitting position by oneself.

The planner fills a name of trainee in the "Exercise administration list".

The planner writes down his or her own name on the "Exercise administration list".

The rehabilitation, muscle power strengthening and thermo therapy prescribed by a planner enables performance in accordance with the planner's itinerary that indicates a trainee and planner specified by entering their names on each of the "Exercise administration list".

If necessary, it is possible to write down a trainee or planner's address when filling their names.

At the time of filling a trainee's name, it is possible to write down age and also records of diseases in the remarks column(s).

The planner authorizes that the trainee can rehabilitate and strengthen muscle power depending on the situation if the trainee can keep a sitting position.

It is possible to change the remarks column(s) to an age, disease record entry column if necessary and to add the age, disease record entry column.

It is also possible to write a daily life independence degree evaluation such as the Functional Independence Measure as an optional evaluation in the remarks column(s).

This is possible even if there is no remarks column.

The specification of a trainee is necessary to define the most suitable rehabilitation and muscle power strengthening for the trainee.

Even if there is no planner, the enrolment of a planner's name in the "Exercise administration list" is effective as the basis that gives the caregiver confidence to perform the rehabilitation by the Takizawa method and the Motivative exercise instead of enforcing the passive exercise for rehabilitation.

It is possible to omit writing a planner's name or omit the planner name column when a planner is clearly decided in the case of using the method in a facility. In the case that a trainee is being rehabilitated at home, it is possible to omit the trainee name column or the trainee name column.

If a trainee has joint contracture and/or flexion, the planner may decide to secure the trainee's sitting position by using cushions.

In an "Exercise administration list", the planner describes the types of exercises such as lower and upper extremities' exercises, a trunk exercise, a standing exercise, a walking exercise and a thermo therapy in detailed exercises columns. And also, the planner distinguishes between assistive exercises and self-training regarding the lower and upper extremities' exercise, the trunk exercise, the standing exercise and the walking exercise.

A thermo therapy may also be described as physiotherapy.

The number of times (Repetitions) of the lower extremities' exercise, the upper extremities' exercise and the trunk exercise, counts per second of the standing exercise and walking distance of the walking exercise are entered in sets of exercise columns.

Furthermore, an exercise of the lower extremities is performed using devices for lower extremities' exercise and an exercise of the upper extremities is performed using devices for upper extremities' exercise.

An abdominal muscle exercise in a sitting position or gymnastics with a wall bar can be selected for a trunk exercise.

The abdominal muscle exercise is usually performed in a sitting position by pushing the body trunk down in front and turning the head down, as if to bow. The abdominal muscle exercise can be performed either as an assistive exercise or self-training.

Wall bar gymnastics are performed securely by using a wall bar.

In sets of exercise columns, the planner lists the following:
- momentum of the exercise by the repetitions of the lower extremities' exercises with each of devices for lower extremities' exercise;
- momentum of the exercise by the repetitions of the upper extremities' exercises with devices for upper extremities' exercise;
- repetitions of the trunk exercises;
- repetitions based on the enforcement of setting in a measure of the seconds for each of the standing exercises; existence of a device for assistive walking in regard to a walking exercise;
- the times of the walking exercises such as the distances of the walking exercises is set in one measure of distance; and
- the time and regions of the thermo therapy defined clearly.

Thereafter the planner entrusts an optional manager to control the rehabilitation exercise as following the "Exercise administration list", which had been listed as consisting of combinations of a trainee name column, a planner name column and exercise columns that consist of detailed exercises columns with types of exercises and sets of exercise columns.

The manager, who is shown the exercise columns consisting of detailed exercises columns and sets of exercise columns in the "Exercise administration list" by the planner, prepares the devices that correspond to the types of exercises listed in the detailed exercises columns for the trainee(s).

Subsequently, the manager specifies and confirms the trainee listed in the trainee name column and confirms for the trainee performing the exercise.

Subsequently the manager correctly organizes the entries of the exercise date column, confirms the remarks column(s) and controls the amount of sets of exercises that are listed in the sets of exercise columns.

When there are an excessive number of trainees to be trained by one manager, the planner assigns different managers to the trainees.

The manager, or a care person, prepares the devices to be used, correctly organizes the entries of the exercise date column and manages the enforcement of the designated amount of the exercise at home.

It is possible that a planner can double as a manager.

In the case that a manager is a planner, it is possible to omit entry of the manager's name when organizing and entering the exercise date column.

Furthermore, lower extremities' exercises can be segmented almost as a front and back reciprocating exercise, a vertically rocking motion exercise and a swing exercise with loading to lower extremities.

Standing exercises can be also segmented in to standing still exercises and gymnastics.

Walking exercises can also be segmented to walking inside parallel bars, types of walkers, walking circumference of parallel bars and stairs training.

Furthermore devices for a thermo therapy can be sufficient if the devices can warm regions of designation.

For example anything such as a warmed towel, a hot pack or a device for microwave irradiation can be used for thermo therapy.

Any kinds of walkers are acceptable for use.

The walkers can be specified not only to describe but also to check mark choosing from many kinds of walkers that are listed.

In the case of segmenting lower extremities' exercises to a front and back reciprocating exercise, a vertically rocking motion exercise and a swing exercise with loading to lower extremities, it is acceptable to segment these exercises by using devices that accommodate the segmented types of exercises.

Exercises such as a range of motion exercise, durability training and a breathing training are included in the types of exercises.

Optionally, individual facilities that perform this invention can change or add the exercises such as a range of motion exercise, durability training and breathing training and change or add the types of the devices.

In the case of adding the exercises such as a range of motion exercise, a durability exercise and a breathing exercise to the detailed exercises columns, it is also possible to manage the enforcement of exercises filling the repetitions in the sets of exercise columns as the following:
- the repetitions of range of motion exercises that are defined in the Takizawa method;
- the repetitions for the durability exercise set up with the devices such as an exercise bike; and the repetitions of deep breathing.

A manager who has been consigned to exercise administration by the planner is able to perform the rehabilitation, muscle power strengthening and thermo therapy that were accurately defined by the planner in the "Exercise administration list" to the trainee(s).

When a manager controls the administration, the manager classifies a trainee who is unable to secure a sitting position into a diseaseful trainee.

In the beginning of the Motivative exercise, physically impaired people who can secure a sitting position do approximately twenty repetitions, usually twenty repetitions for both a front and back reciprocating exercise and a vertically rocking motion exercise.

A pulling capacity of 0.5 kg or 1 kg with twenty repetitions are suitable for a lower extremities' load and swing exercise, which are a lower extremities' exercise that is carried out under the condition that a knee joint is pulled downward.

In the case of providing a remarks column(s) enabled filling the repetition changes, it is possible to print repetitions of exercises in the sets of exercise columns in advance.

Devices to load tractional force are weight bands for the swing exercise.

Although anything is acceptable without limiting to a weight band for devices that are able to haul a knee joint downward when used for the swing exercise.

Devices for upper extremities' exercise are used for an upper extremities' exercise.

When training starts, twenty repetitions of an upper extremities' exercise are suitable.

In the case of providing a remarks column(s) enabled writing down the repetition changes, it is possible to print repetitions of an upper extremities' exercise in the sets of exercise column in advance.

With regards to the exercises, ten repetitions may be suitable about one week from the beginning.

In the situation where physical conditions are improved and walking becomes possible, approximately fifty repetitions may be suitable.

A thermo therapy usually warms up joints.

For example, it is possible to print words such as shoulders (right and left), elbows (right and left) and knees (right and left) in the sets of exercise column in advance in order to use the words by marking to specify the area.

The standing exercise is in ten-second units and it is also possible to write down the repetitions of the enforcement number.

A manager usually assists a trainee at the time of the standing exercise.

In the case of enforcing exercises at home, a care person usually assists a trainee(s).

A walking exercise is performed after the trainee is able to stand, but a manager assists the trainee in the beginning.

The trainee performs the front and back walking inside the parallel bars.

Usually the parallel bars are 6 m long and it is possible to fill the repetitions of round trips in the sets of exercise column.

In the case of a trainee(s) enabled walking by oneself in the parallel bars, it is possible to fill the repetitions of round trips of the parallel bars by segmenting forward walking, crosswise walking and backward walking.

Through exercises at home, it is possible to perform the walking exercise under the manager's indication of the repetitions of round trips of the parallel bars' distance by securing the safety of a trainee like using parallel bars.

Ten times of repetitions are preferable and recommended to perform the range of motion exercise in the Takizawa method and deep breathing training.

The repetitions of these exercises should be adjusted accordingly for healthy trainees who are suitable for durability training.

Of course, it is possible to decide repetitions of the range of motion exercise and deep breathing training in the Takizawa method.

It is possible not to fill directions concerning a standing exercise of the trainee who can perform a walking exercise.

It is possible to omit writing about a standing exercise of the trainee who can perform a walking exercise.

It is possible to perform a trunk exercise by the repetitions of the abdominal muscle exercise as a unit.

The abdominal muscle exercise can be performed either as an assistive exercise or as self-training.

It is possible to perform a trunk exercise by designating repetitions of wall bar exercises specified as a unit.

When a trainee can walk inside the parallel bars, a device to assist walking is selected.

There are cases to use devices to assist walking is not necessary.

The trainee can perform the exercise on the basis of circumference distance of 6 m of the parallel bars, even in the either case that they use any devices for assistive walking or they do not use any devices to assist walking.

It is possible to perform the exercise with the indication of repetitions on the basis of circumference distance of 6 m of the parallel bars.

This embodiment of this invention is shown above.

Therefore, one manager can confidently perform the rehabilitation and muscle power strengthening and/or the Takizawa method and the Motivative exercise to many trainees.

And in the case where a manager is a doctor, physical therapist or other kind of therapist for rehabilitation, the manager can control to perform rehabilitation and muscle power strengthening as well as the medical chart entry by filling an exercise date in the exercise date column of the "Exercise administration list" and matters of special mention in the remarks column(s).

And a manager can manage the rehabilitation and muscle power strengthening by filling an exercise date in the exercise date column of the "Exercise administration list" and matters of special mention in the remarks column(s).

When a manager must rehabilitate an excessive number of trainees, additional managers can aid to control rehabilitation.

A caregiver can control trainee(s)'s rehabilitation exercises at home in accordance with an "Exercise administration list".

Trainees are controlled by a manager in this way correctly and safely.

In other words, summary of mentioned above shown as follows:

A planner, who is a specialist, specifies an optional trainee(s), decides contents of the rehabilitation and muscle power strengthening, fills the specified exercises in the "Exercise administration list" and delivers the "Exercise administration list" to any optional manager;

Otherwise, a planner, who decides contents of the Takizawa method and the Motivative exercise and fills decided contents in an "Exercise administration list", delivers the "Exercise administration list" to the optional manager;

When there is an excessive amount of trainees for one manager to control, the planner entrusts optional numbers of manager(s) and assigns optional numbers of trainees to the manager(s) with using the "Exercise administration list";

Subsequently, the manager supervises the exercise enforcement of the trainee;

Thereafter, in the condition of one manager to many trainees, the trainee can perform the rehabilitation and muscle power strengthening and/or the Takizawa method and the Motivative exercise that substitute for the rehabilitation by one physical therapist to one patient as ease;

And also the trainee can perform the rehabilitation and muscle power strengthening and/or the Takizawa method and the Motivative exercise with following the "Exercise administration list" by oneself or with assistances of a caregiver;

At the time assisting to perform rehabilitation, the caregiver can assist without anxiety that arises when the caregiver performs a rehabilitation exercise such as a passive exercise in accordance with specialist's directions at home;

Then to confirm the enforcement of the exercise according to the "Exercise administration list", a manager fills the exercise date in the exercise date column of the "Exercise administration list", and fills matters for special mention in the remarks column(s) such as memo column.

Though physical therapists have enforced rehabilitation exercises as follows:

by checking the physical conditions of a patient (trainee) and then deciding the contents of physical therapies according to the doctor's directions and prescription;

thinking in their knowledge every time to build up contents of physical therapies and to decide it to individual patients; and filling a medical chart about this confirmation and arrangement, this invention can simplify checking the physical conditions and can reduce the labor of thinking contents and filling the medical chart for the enforcement of rehabilitation for physical therapist.

This applicant describes the second embodiment of this invention as following.

First, this embodiment is composed of an "Exercise control list" and "Performing days list" and is used for the control of the Takizawa method and the Motivative exercise and the rehabilitation and muscle power strengthening.

Takizawa method is enable one manager to rehabilitate many trainees.

There are many cases that a planner controls exercises as one of manager in optional numbers of managers concerning actual operation.

An exercise administration list is a document that named "Exercise control list", consists of a "name column" and "exercise columns" that are laid out properly for use in this embodiment.

The name column consists of a "trainee name column" and a "planner name column".

The exercise columns consist of "detailed exercises columns" with the types of exercises that are set up in multiple steps, in which a type of exercises and/or a type of thermo therapy is listed and "sets of exercise columns" that are set up in multiple steps, in which momentum are mentioned.

A part and enforcement time to the thermo therapy in the Takizawa method and a measure and a number of times to kinetic momentum of the exercise are indicated clearly in the sets of exercise columns.

Then, the exercise columns include detailed exercises columns with the types of exercises and sets of exercise columns, which are laid out properly, in each set.

A document that is named "Performing days list", in which "name columns", "exercise date columns" and "remarks columns" are laid out properly, is another document.

Name columns that are set up in multiple steps are "trainee name columns" of the rehabilitation and muscle power strengthening.

Exercise date columns consist of multiple rows of "date of exercise columns" and "manager(s) name columns".

The exercise date column consists of sets both the date of exercise column and the manager(s) name column.

Remarks columns, for memos are laid out near the name columns and/or the date of exercise columns appropriate notation.

Detailed exercises columns with the types of exercises in the "Exercise control list" are set up in multiple steps.

Then PATAKORO, belts, pulleys, hot packs, the parallel bars, stairs and abdominal muscles/wall bars gymnastics is described in the detailed exercises columns with the types of exercises and a type of thermo therapy.

In other words "PATAKORO and weight belts for the lower extremities' exercise, pulleys for the upper extremities' exercise, hot packs for the thermo therapy, the parallel bars for the standing and walking exercise, stairs for the walking exercise and abdominal muscles/wall bars gymnastics for the trunk exercise" are contents. And then, the time and regions of the thermo therapy and time, measure of kinetic momentum and a number of times are written down for sets of the exercise in the sets of exercise columns are "20 times, a number 0.5 kg×20 time and 1 kg×20 time, 20 times, shoulders (right and left) elbows (right and left) knees (right and left) thighs (right and left), the stand exercise 1 time 2 times forward 1 time 2 times backward 1 time 2 times sideward 1 time 2 times circumferential 1 time 2 times, low 1 time 2 times high 1 time 2 times, the number of time" to write.

In other words, the exercise columns that consist of the combination of the detailed exercises columns and the sets of exercise columns are "PATAKORO 20 times, belts 0.5 kg×20 time/1 kg×20 time, pulleys 20 times, hot packs shoulders (right and left) elbows (right and left) knees (right and left) thighs (right and left), the parallel bars/the stand exercise 1 time 2 times forward 1 time 2 times backward 1 time 2 times sideward 1 time 2 times circumferential 1 time 2 times, stairs low 1 time 2 times/high 1 time 2 times and the abdominal muscles/wall bars gymnastics the number of time to write".

And, the rehabilitation and muscle power strengthening is managed, depending on the steps of a procedure and technique and follows the "Exercise control list" and the "Performing days list".

A planner specifies an optional trainee and confirms that the trainee is able to maintain a sitting position by oneself.

The planner writes down his/her full name and the full name of a trainee who is rehabilitated or rehabilitates and/or trains muscles in the "Exercise control list".

The planner or a manager who is entrusted to control the training by the planner writes down the full name of the trainee in the "Performing days list".

"Performing days list" has name columns where the names of trainees, who are specified by the "Exercise control list" are listed, there are the name columns for the trainees that are set up in multiple steps in "Performing days list".

A planner or a manager can list the full names of many trainees who were specified in the name columns that are set up in multiple steps.

When there is an excessive amount of trainees to be trained by one manager, the planner assigns different managers to the trainees.

Furthermore, it is possible that a planner or a manager who is directed by a planner make any assistants take dictation in order to fill comment in the "Exercise control list" and the "Performing days list".

The rehabilitation, muscle power strengthening and thermo therapy can be performed in accordance with the planner's itinerary that indicates a trainee and planner specified by name of the trainee and planner in the "Exercise control list".

The planner authorizes that the trainee can rehabilitate and strengthen muscle power if the trainee being able to maintain a sitting position.

In the case where the planner determines the trainee's ability to be in a sitting position, cushions may be used to maintain a sitting position, if necessary, since they have joint contracture and flexion.

In this way a planner and a trainee are specified, the rehabilitation, muscle power strengthening and thermo therapy can be carried out in accordance with the planner's itinerary.

If necessary, it is possible to write down address and age besides a name of a trainee in the trainee name columns of the rehabilitation and muscle power strengthening of "Performing days list".

If necessary, it is possible to write down the disease record of the trainee in the remarks columns of "Performing days list".

In the case where many trainees exercise at the same time, it is necessary to specify the trainee so that a manager enforces individual trainees to perform the most suitable rehabilitation and muscular force training.

If a planner is solely used in a facility, it is possible to omit writing a planners name in the planner(s) name column or it is possible to omit the planner name(s) column. In the indication of this embodiment, PATAKORO 20 times, weight belts 0.5 kg×20 time/1 kg×20 time, pulleys 20 times, hot packs shoulders (right and left) elbows (right and left) knees (right and left) thighs (right and left), the parallel bars/the stand exercise 1 time 2 times forward 1 time 2 times backward 1 time 2 times sideward 1 time 2 times circumferential 1 time 2 times, stairs low 1 time 2 times/high 1 time 2 times, abdominal muscles/wall bars gymnastics the number of time to write, the words show as follows;

PATAKORO 20 times shows 20 times exercises with using both the devices for vertically rocking on lower extremities' function training, named PATAPATA, the design patent registered JP 1096056 LOWER EXTREMITYS FUNCTION TRAINING DEVICE and the devices for front and back reciprocating on lower extremities function training, named KOROKORO, the registration of utility model JP 2004587 DEVICE OF DORSIFLEXION AND PLANTAR FLEXION OF ANKLES AND KNEES, PATAKORO shows the exercises by the design patent registered JP 1096056 and the registration of utility model JP 2004587, weight belts 0.5 kg×20 time/1 kg×20 time shows 20 times the swing exercise of a lower extremity with winding weight bands on the market around the ankle and load 0.5 kg or 1 kg downward, pulleys 20 times shows 20 times the exercise of a upper extremity with patents request PCT/JP00/04062 MOTIVATIVE EXERCISE AND LIFTING AID DUAL DEVICE, a device of assembling-type on upper extremities' training and a part of the device on upper extremities' training that was applied patent in which number is undecided, Hot packs are used for thermo therapy to warm the necessary regions such as shoulders (right and left) elbows (right and left) knees (right and left) thighs (right and left) using devices to warm, parallel bars/the stand exercise 1 time 2 times shows that the trainee who could keep only sitting position, and who is able to keep standing position in result of exercises or to use the devices such as the registration of utility model JP 1901372 FOOT BRACE, the design patent registered JP 882110 MEDICAL SOCK and/or a device devised for knee patch performs 1 time or 2 times of the standing exercise in ten-second units, parallel bars/forward 1 time 2 times shows that a trainee who is able to perform the standing exercise possible performs 1 time or 2 times of the reciprocating walking exercises by facing in forward in a measure of the distance of the parallel bars with the support of the parallel bars, parallel bars/backward 1 time 2 times shows that a trainee who is able to perform the parallel bars/the forward walking exercise possible performs 1 time or 2 times of the reciprocating backward inclined walking exercises with facing forward in a measure of the distance of a parallel bars with a support of the parallel bars, parallel bars/sideward 1 time 2 times shows that a trainee who is able to perform the parallel bars/the forward walking exercises performs 1 time or 2 times of the reciprocating sideward walking exercises by facing in forward in a measure of the distance of the parallel bars with the support of the parallel bars, parallel bars/circumferential 1 time 2 times shows that a trainee who is able to perform the parallel bars walking exercise possible performs 1 time or 2 times of the circumference of a parallel bars' walking exercises with help of devices such as the registration of utility model JP 1895489 WALKER or the design patent registered JP 952134 WALKER or without any help of devices if not necessary, stairs low 1 time 2 times shows a trainee who is able to walk performs 1 time or 2 times of the up down walking stairs exercises of height 72 cm by six-steps stairs, stairs high 1 time 2 times shows that a trainee who is able to walk performs 1 time or 2 times of the up-down walking stairs exercises of height 72 cm by four-steps stairs, abdominal muscle gymnastics is a trunk exercise where a trainee moves his or her own trunk forwards and backwards like bowing and a numbers of the times of an abdominal muscle exercise is decided individually and wall bars gymnastics is a trunk exercise that is performed according to the decided numbers of repetitions.

The concept of both the Takizawa method and the Motivative exercise has recently been acknowledged, devices that enable exercises such as upper extremities' exercises and lower extremities' exercises have been developed as;

the patent application H11-358206 Lower extremities exercise device, the patent application 2000-180958 Motivative exercise device for lower extremities, the patent application PCT/JP99/07115 Lower extremities exercise device and the patent application PCT/JP00/03978 Motivative exercise device for lower extremities.

There are a few academic presentations that examine both the Takizawa method and the Motivative exercise and all of devices in both the Takizawa method and the Motivative exercise have not been confirmed.

The devices to be used in this embodiment are examples and other effective devices may be used.

Therefore, the devices in this embodiment are not limited as used devices of this invention.

In the second embodiment, it is possible to write down a type of the exercises as a front and back reciprocating, a vertically rocking and a load lower extremities' exercise, upper extremities' exercises, thermo therapy, the parallel bars, stairs and trunk training in the detailed exercises columns that are set up in multiple steps and 20 times, 0.5 kg×20 time and 1 kg×20 time, 20 times, shoulders (right and left)/elbows (right and left)/knees (right and left)/thighs (right and left), the stand exercise 1 time 2 times/forward 1 time 2 times/backward 1 time 2 times/sideward 1 time 2 times/circumferential 1 time 2 times, /low 1 time 2 times/ high 1 time 2 times, abdominal muscle/wall bar the number of time, regions of the thermo therapy, time and measure of kinetic momentum and a number of times in the sets of exercise columns.

A thermo therapy may be written as physiotherapy.

In other words, it is possible to describe front and back reciprocating, vertically rocking lower extremities 20 times, the load lower extremities' exercise 0.5 kg×20 time/1 kg×20 time, the upper extremities' exercises 20 times, thermo therapy shoulders (right and left)/elbows (right and left)/ knees (right and left)/thighs (right and left), the parallel bars standing exercise 1 time 2 times/forward 1 time 2 times/ backward 1 time 2 times/sideward 1 time 2 times/circumferential 1 time 2 times, stairs low 1 time 2 times/high 1 time 2 times, trunk training abdominal muscle/wall bar the number of time, regions of the thermo therapy, time and measure of kinetic momentum and a number of times in the exercise columns in the "Exercise control list".

The specified exercise repetitions are rough standards that can be changed according to a trainee's needs.

When a manager must train an excessive number of trainees, the planner assigns different managers to the trainees.

And the planner can write down;

lower extremities' exercises that can be segmented a front and back reciprocating exercise, a vertically rocking exercise and a load and swing exercise;

standing exercises can be segmented standing keeping and gymnastics;

and walking exercises can be segmented walking in a parallel bars, types of walker, circumferential walking and stairs walking;

in the detailed exercises columns with the types of exercises that are set up in multiple steps that have types of exercises and thermo therapy.

It is possible to write down a kinetic exercise momentum that is specified of the types of exercises in the sets of exercise columns with accommodating types of exercises that are described in the detailed exercises columns with the types of exercises that are segmented.

And, it is possible that the exercise columns consist of the combination of the sets of exercise columns that accommodate to types of exercises and types of thermo therapy that was written down in the detailed exercises columns with the types of exercises as well as the first embodiment.

Furthermore devices for thermo therapy can be sufficient if the devices can warm regions.

It is also possible that the exercise enforcement is managed by listing a number of times of range of motion exercises that are performed as defined in the Takizawa method, the number of times that the amount of a setup the exercise with the devices such as an exercise bike for durability training such as the number of times of deep breathing in the sets of exercise columns, such as range of motion exercises, durability training and breathe training were added in the detailed exercises columns as well as the first embodiment.

A manager who has been consigned the exercise administration by the planner is able to perform the rehabilitation, muscle power strengthening and thermo therapy that were accurately defined by the planner in the "Exercise control list" to the trainee(s).

When a manager controls the administration, the manager classifies a trainee who is unable to secure a sitting position into a diseaseful trainee.

A manager who is shown the exercise group column consisting of the detailed exercises columns and the sets of exercise columns by the planner, prepares the devices that correspond to the types of exercises listed in the detailed exercises columns with the types of exercises.

The devices to be used are mentioned in the previous items in this embodiment.

Subsequently, the manager specifies the trainee by confirming the trainee name column.

Subsequently the manager manages enforcement of the amount of sets of exercise that are listed in the sets of exercise columns to the trainee.

It is possible that a planner can double as a manager.

In the case where a planner doubles as a manager, there are many cases that a planner controls exercises as a manager of the inside one optional number of managers.

Subsequently the manager correctly organizes and entries on the exercise date column, with confirming the trainee name columns with using "Performing days list".

When many trainees are managed at the same time, an exercise date is written down in one-step of the exercise date columns (usually, the column of the extreme front) and then it is possible correctly to organize and to write down a mark that means enforcement in an applicable step on the exercise date of the other trainee in the exercise date columns.

In the case of making the mark peculiar to the individual manager, the mark can substitute for the description of the name of the manager.

To stamp in the exercise date column can substitute for the description of the name of the manager as well.

In this case, the name of the manager column(s) may be omitted as well.

In the case that a manager is the planner, it is possible to omit entry of the manager's name when organizing and entering an exercise date column.

Remarks columns are composed for writing down matters for special mention that are related for both a trainee and an exercise date or either a trainee or an exercise date, it is good even if it is not specially set up in the case of writing memo of the matters for special mention in the trainee name columns or the exercise date columns.

The manager who was consigned the exercise administration with the planner is able to control the rehabilitation, the muscle power strengthening and thermo therapy, that were accurately defined by the planner such that the trainee works their rehabilitation, as they clearly described those to the "Exercise control list".

When the manager controls the administration, the manager classifies a trainee who has a body dysfunction and is unable to secure a sitting position.

It is possible not to fill directions concerning a standing exercise of the trainee who can perform a walking exercise.

It is possible to omit writing about the standing exercise for the trainee who can perform the walking exercise.

Managers assure trainees to rehabilitate and strengthen muscle power correctly and safely.

In other words, the summary of the above mentioned steps are as follows:

A planner who is a specialist specifies an optional trainee, decides contents of the rehabilitation and muscle power strengthening and/or the Takizawa method and the Motivative exercise, writes down them in the "Exercise control list" and delivered the "Exercise control list" and an "Performing days list" to an optional manager.

Subsequently, the manager supervises the trainee.

Thereafter, the trainee can perform the Takizawa method and the Motivative exercise and/or the rehabilitation and muscle power strengthening, which substitute for the rehabilitation of one physical therapist to one patient comfortable in the condition of one manager to many trainees as well as a passive exercise in the rehabilitation of one physical therapist to one patient.

When a manager must train an excessive amount of trainees, the planner assigns different managers to the trainees under exercise.

And also a trainee can perform rehabilitation and muscle power strengthening and/or the Takizawa method and The Motivative exercise at home by following the "Exercise control list" by oneself or with assistances of the caregiver without performing a passive exercise without anxiety.

Then the manager, who is directed by the planner, confirms the enforcement of the exercise that conforms to the "Exercise control list".

Thereafter, the manager lists an exercise date in one-step of the exercise date column, and the exercise date columns are set up in multiple steps in the "performing days list".

Physical therapists decide the contents of rehabilitation according to a doctor's directions and prescription and enforce the rehabilitation exercise by checking physical conditions of a patient.

Physical therapists use their knowledge to compose the contents of rehabilitation exercise for individual patients and fill a medical rehabilitation chart containing and confirming this arrangement.

This invention can reduce the labor of filling the chart after the enforcement of rehabilitation for physical therapist.

There is the above-mentioned process in the embodiment.

Therefore many persons exercise by one administrator confidently when the rehabilitation and muscle power strengthening and/or Takizawa method and the Motivative exercise are performed.

A manager writes down an exercise date with using a "Performing days list" and writes down matters for special mention in the remarks column as well as the "Exercise administration list" of the first embodiment if necessary.

Therefore a manager, such as a doctor or physical therapist, can omit the complexity of the medical chart entry and can control the rehabilitation and muscular power strength training centering and/or the Takizawa method and the Motivative exercise.

A caregiver is able to perform and to control an exercise of a trainee in accordance with an "Exercise control list" at home.

Furthermore, it is possible to name the name columns only "name" in the first embodiment and the second embodiment.

Also, the exercise date columns may be named "date".

A planner name column is as well possible to make "charge".

Detailed exercises columns is as well possible to make "exercise" and "sets of exercise columns" is as well possible to make "amount", or it is possible to not describe such as "time", "amount" or "unit of distance" if units are evident.

In other words, names of columns body forth meaning that has an idea, therefore it is possible to name any kind of names if column can show the meaning.

Also, there is the place where devices of exercises are prepared in advance in optional facilities.

In the case of enforcing and administrating by this invention in the facilities, it is possible to perform the rehabilitation and muscle power strengthening and/or the Takizawa method and the Motivative exercise out of order that shows in this embodiment, for example, an order such as the manager confirms the exercise working contents for each trainee, prepares necessary devices and then confirm the exercise date thereafter, the manager can control the exercises of each trainee.

Although the length of the parallel bars is described with 6 m, the length of devices may be changed, as an example, it is possible to use the parallel bars of 4 m as well.

It is sufficient to indicate a number that is converted the length to the standard value of 6 m.

Although the stairs made the height of 72 cm a standard, the height of application may be changed and it is possible to use the height that is converted on the basis of this height.

Use Possibility in Industry

This invention enables a trainee including the elderly and physically impaired people who require the rehabilitation with physical therapies to recover and improves and/or strengthens a body's impaired function.

Additionally, this is a Control System of training by the Takizawa method and the Motivative exercise for an elderly and/or a physically impaired person.

This invention can dissolve the hard burden that physical therapists who examine variously based on the doctor's directions and think with the knowledge for each patient every time to build up contents of the rehabilitation with physical therapies and both doctors and physical therapists write down a medical rehabilitation chart with handwriting every time.

It is possible to reduce expenses by reducing the number of physical therapists because one manager can control and rehabilitate several trainees (patients) enforcing exercises that center on the Takizawa method and the Motivative exercise instead of the rehabilitation with physical therapies heretofore with this invention.

In the case that caregivers rehabilitate a care needed person (trainee) at home, if it is not possible for trainees to perform active exercises, the caregiver with the advice of a physician and/or a physical therapist has performed the passive exercise.

According to this invention, trainees can rehabilitate by performing the Motivative exercise that a healthy extremity leads an impaired extremity of trainees using devices themselves by the Takizawa method and the Motivative exercise and/or muscular power strength training because of receiving directions from a planner clearly by using the list that shows the Takizawa method and the Motivative exercise to rehabilitate.

Therefore, it is possible for caregivers to dissolve the burden of performing rehabilitation and anxiety such as performing a passive exercise.

And also caregivers can perform and control an assisted training by assisting the movement of a device correctly and safely.

According to the explanation, the invention has practical that can dissolve the burden of doctors and physical therapists.

This is practical, as costs will be reduced because fewer physical therapists are needed.

Furthermore, an at home caregiver's anxiety can be relieved when the patient (trainee) can use the devices without active help from the caregiver.

The invention claimed is:

1. A method for controlling rehabilitation and muscle power strength training, comprising:
   (i) providing at least one first list having columns each including:
      one of said columns for a name of said trainee who is an old and/or physically impaired person in need of individual rehabilitation by physical therapy, and
      two or more of said columns for kinds of exercises defined by at least a name of each exercise and number of repetitions or duration of each exercise, said exercise being selected from the group consisting of:
      exercises of upper extremities and number of repetition,
      exercises of a body trunk and number of repetition,
      exercises of lower extremities and number of repetition,
      exercise with a hot pack or hot packs, length of enforcement time period and place,
      exercises with parallel bars and number of repetition, and
      exercises with steps and number of repetition;
   (ii) planning for a trainee kinds of exercises defined by at least a name of each exercise and number of repetition or duration of each exercise for rehabilitation and muscle power strengthening;
   (iii) filing the first list by:
      indicating a name of said trainee in the column for trainee, and
      indicating kinds of exercises for said trainee defined by the name of exercise and the number of repetition or duration in each of said columns for kinds of exercises;
   (iv) providing a second list having columns including:
      at least one of said columns for one or more trainees' names including the one specified in the first list,
      at least one of said columns for dates for performing the exercises specified in the first list,
      at least one of said columns for at least one manager's name, wherein said manager is to fill the second list and to indicate, supervise or assist rehabilitation and muscle power strengthening of the one or more trainees specified by the manager to perform the exercises;
   (v) filling the second list by
      indicating one or more trainees' names including the one specified in the first list,
      indicating a date of performing the exercises specified in the first list, and
      indicating at least one manager's name; and
   (vi) managing the exercises specified in the first list for the trainee and confirming or arranging a date of performing the exercises in said second list.

2. A method for managing rehabilitation and muscle power strengthening by a working program and motivative exercises, comprising:
   (i) providing at least one first list having columns each including:
      one of said columns for a name of a trainee who is an old and/or physically impaired person in need of individual rehabilitation by physical therapy, and
      two or more of said columns for kinds of exercises defined by at least a name of each exercise and number of repetition or duration of each exercise, said exercise being selected from the group consisting of:
      exercises of upper extremities and number of repetitions,
      exercises of a body trunk as bowing and number of repetition,
      exercises of lower extremities to move front and back reciprocating and number of repetition,
      exercises of lower extremities to move vertically rocking and number of repetition,
      exercises of lower extremities to swing with loading weight, weight and number or repetition,
      exercises with a hot pack or hot packs, length of enforcement time period and place,
      exercises with parallel bars or wall bars for standing and number of repetition,
      exercises with parallel bars or wall bars for force walking and number of repetition,
      exercises with parallel bars or wall bars for reverse walking and number of repetition,
      exercises with parallel bars or wall bars for transverse walking and number of repetition,
      exercises of walking in a circle around parallel bars, number of repetition and a kind of walkers and
      exercises of walking with steps and number or repetition;
   (ii) planning for a trainee kinds of exercises defined by at least a name of each exercise and number of repetition or duration of each exercise for rehabilitation and muscle power strengthening;
   (iii) filing the first list by
      indicating a name of said trainee in the column for trainee, and
      indicating the kinds of exercises defined by the name of exercise and the number of repetition or duration in each of said column for kinds of exercises;
   (iv) providing a second list having columns including:
      at least one of said columns for one or more trainees' names specified in the first list,
      at least one of said columns for dates for performing the exercises specified in the first list, and
      at least one of said columns for at least one manager's name, wherein said manager is to fill the second list and to indicate, supervise or assist rehabilitation and muscle power strengthening of the one or more trainees specified by the manager to perform the exercises;
   (v) filling the second list by
      indicating one or more trainees' names specified in the first list, indicating a date of performing the exercises specified in the first list, and indicating at least one manager's name; and (vi) managing the exercises specified in the first list for the trainee and confirming or arranging a date of performing the exercises in said second list.

3. A method for managing exercise for function recovery and muscle strengthening, comprising:

obtaining a plurality of exercise administration lists each containing a name column and an exercise group column that is divided in several kinds of columns of exercises for function recovery and muscle strengthening, each exercise administration list identifying an exercise person in the name column in need of exercise and a group of exercises for the person in the exercise group column;

obtaining an exercise date list containing an name column composed of multiple rows and an exercise date column composed of multiple rows;

inputting in the name column of the exercise date list multiple names of exercise persons identified in the exercise administration lists;

confirming exercise working contents for the exercise persons based on the exercise administration lists;

arranging devices used for performing the exercise working contents;

confirming the names of the exercise persons based on the exercise date list;

managing the exercises of the multiple exercise persons for function recovery and muscle strengthening based on the exercise administration list; and inputting the date of exercise in the exercise date column of the exercise date list.

4. The method according to claim 3, wherein the exercise person is an elderly patient who is in a disuse syndrome and has impairments, the exercises indicated in the exercise group column is motivative exercises, and the exercise group column further includes a working program for function recovery and muscular power strength exercise that centers around the motivative exercises for the elderly patient, wherein the managing step comprises managing the motivative exercises and the working program.

5. The method according to claim 1, further comprising repeating steps (i)–(iii) to prepare multiple first lists each for a different trainee, wherein the second list includes the names of the multiple trainees specified in the fist lists for managing the exercises for the multiple trainees in step (vi).

6. The method according to claim 2, further comprising repeating steps (i)–(iii) to prepare multiple first lists each for a different trainee, wherein the second list includes the names of the multiple trainees specified in the fist lists for managing the exercises for the multiple trainees in step (vi).

7. The method according to claim 3, further comprising appointing an exercise administrator for managing exercise, wherein the exercise date column of the exercise date list further contains a name column for indicating the name of the exercise administrator.

8. The method according to claim 3, wherein the step of managing the exercises comprises managing the exercises of the multiple exercise persons simultaneously.

9. The method according to claim 3, wherein the step of managing the exercises comprises managing the exercises of the multiple exercise persons singly.

* * * * *